United States Patent [19]

Dodge

[11] Patent Number: 5,429,485
[45] Date of Patent: Jul. 4, 1995

[54] PLURAL INLET PUMPING CASSETTE WITH INTEGRAL MANIFOLD

[75] Inventor: Larry H. Dodge, River Falls, Wis.

[73] Assignee: Minnesota Mining and Manufacturing Company, St. Paul, Minn.

[21] Appl. No.: 269,953

[22] Filed: Jun. 30, 1994

Related U.S. Application Data

[63] Continuation of Ser. No. 993,104, Dec. 18, 1992, abandoned.

[51] Int. Cl.⁶ .................. F04B 43/00; F04B 39/00
[52] U.S. Cl. .................. 417/442; 417/479; 417/505; 417/478; 137/606; 604/152; 604/153; 604/258; 128/DIG. 12
[58] Field of Search .......... 417/300, 302, 442, 479, 417/505, 522, 557, 478; 137/606; 604/151, 152, 153, 258; 28/DIG. 12

[56] References Cited

U.S. PATENT DOCUMENTS

| | | |
|---|---|---|
| 3,566,930 | 3/1971 | Kirschner . |
| 4,236,880 | 12/1980 | Archibald ............ 417/478 |
| 4,382,753 | 5/1983 | Archibald ............ 417/479 |
| 4,512,764 | 4/1985 | Wunsch ............... 604/80 |
| 4,657,490 | 4/1987 | Abbott ................ 417/505 |
| 4,696,671 | 9/1987 | Epstein et al. . |
| 4,710,166 | 12/1987 | Thompson et al. . |
| 4,713,063 | 12/1987 | Krumme ............. 604/250 |
| 4,823,833 | 4/1989 | Hogan et al. . |
| 4,838,856 | 6/1989 | Mulreany et al. . |
| 4,865,584 | 9/1989 | Epstein et al. ........ 604/258 |
| 4,925,444 | 5/1990 | Orkin et al. .......... 604/80 |
| 5,047,012 | 9/1991 | Leuschner et al. . |
| 5,062,774 | 11/1991 | Kramer et al. ........ 417/479 |
| 5,108,367 | 4/1992 | Epstein et al. ........ 128/DIG. 12 |
| 5,163,902 | 11/1992 | Lynn et al. .......... 604/86 |
| 5,190,525 | 3/1993 | Oswald et al. ....... 604/83 |
| 5,192,269 | 3/1993 | Poli et al. ............ 604/82 |
| 5,207,642 | 5/1993 | Orkin et al. . |
| 5,304,126 | 4/1994 | Epstein et al. . |

FOREIGN PATENT DOCUMENTS 0288716 11/1988 European Pat. Off. .
0293592 12/1988 European Pat. Off. .

OTHER PUBLICATIONS

U.S. patent application No. 07/926,826, filed Dec. 13, 1990, To Nornberg et al.

Primary Examiner—Richard A. Bertsch
Assistant Examiner—Roland G. McAndrews, Jr.
Attorney, Agent, or Firm—Gary L. Griswold; Walter N. Kirn; Stephen W. Bauer

[57] ABSTRACT

An integral disposable manifold and pump cassette, through which fluid is pumped from inlet tubes, forms a single disposable cassette which may be inserted into a single pump housing. The integral disposable manifold and pump cassette includes first and second sheets of flexible plastic material. Sealed inlet channels are formed between the first and second sheets of flexible plastic material, with the sealed inlet channels being connectable to inlet tubes for fluid passage therethrough. The sealed inlet channels can be individually pinched off to prevent fluid passage therethrough. A sealed main channel, which is connected between the inlet channels and an outlet tube is formed between the first and second sheets of flexible plastic material. The sealed main channel includes a pumping chamber which is also formed between the first and second sheets of flexible plastic material. A flange, also formed between the first and second sheets of flexible plastic material, generally surrounds the inlet channels and the main channel. The flange facilitates the insertion and removable of the disposable manifold and pump cassette from the single pump housing. A first flexible diaphragm, extending outward from the flange, is formed in the first sheet of flexible plastic material. The first flexible diaphragm forms a portion of the pumping chamber.

22 Claims, 3 Drawing Sheets

PLURAL INLET PUMPING CASSETTE WITH INTEGRAL MANIFOLD

This is a continuation of application Ser. No. 07/993,104 filed Dec. 18, 1992, now abandoned.

BACKGROUND OF THE INVENTION

The present invention relates to volumetric infusion pumps for the administration of intravenous (IV) fluids to a patient. More particularly, the invention relates to a disposable soft manifold and pump cassette for supplying a plurality of solutions to one or more intravenous tubes.

Intravenous infusion therapy involves the administration of medications and other fluids directly into the circulatory system of a patient. Infusion pumps are typically used to regulate the delivery of these medications and fluids with a high degree of accuracy. Medical treatment frequently requires the administration of more than one solution or medication to an individual patient. In many medical treatments, several drugs are administered sequentially or periodically. Alternatively, a patient may need a particularly large volume of a single infused liquid requiring more than one supply vessel, or may need to have two or more different solutions delivered in rapid succession, solutions which would lose their efficacy if mixed.

In early attempts to administer multiple fluids to a patient, plural independent gravity flow controllers and plural independent electronic pumps have been employed. Both of these methods of administering multiple fluids to a patient have significant disadvantages. For example, both methods require the use of multiple IV tubes to administer the fluids, resulting in multiple IV venipuncture and a corresponding increased risk of infection. Also, both the plural gravity flow controller method and the plural electronic pump method result in considerable increased clutter around the patient and increased time and labor by the health care practitioner to set up and operate. Plural gravity flow controllers have the additional disadvantage of being prone to inaccuracies due to tube occlusion or shape changes. Likewise, plural independent pump methods have additional disadvantages including the high cost of maintaining several pumps for each patient, and of maintaining an inventory of tubes that must be replaced periodically to avoid infection.

The prior art has employed several methods in attempts to overcome these mentioned difficulties. Many of the prior art methods involve the use of disposable cassettes or manifolds with multiple fluid inlet channels to accommodate a plurality of solutions. However, these prior art disposable cassettes and manifolds have their own disadvantages which the present invention overcomes.

Epstein et al., U.S. Pat. No. 4,696,671, discloses an infusion system for administering multiple infusates at individually programmable rates and sequences. In Epstein, a disposable cassette with plural fluid input ports and one fluid output port is provided. All fluids flow through this unitary disposable cassette without making any other system contact. The multiple input port disposable cassette disclosed in Epstein eliminates many of the difficulties discussed above, including the risk of infection due to multiple IV punctures since only a single IV puncture is necessary. The Epstein cassette also eliminates some of the increased time, labor, and cost required to maintain multiple gravity flow controllers or independent electronic pumps.

However, the construction of the disposable cassette disclosed in Epstein has disadvantages as well. This design involves rigid injection molded parts. The rigid molded construction introduces several disadvantages. First, the rigid construction results in higher labor and assembly costs, which increases the cost to the health care consumer. A second disadvantage of the disposable cassette disclosed in Epstein relates to the control of fluid flow through different input ports. Cassettes of this type typically employ solenoid valves or motor-driven actuators to pinch off tubing in a sequential manner in order to restrict or control fluid flow. Pinching off the rigid tubing disclosed in Epstein requires considerable force, and consequently considerable energy. In addition to being energy inefficient, these forces can also have an adverse affect on the tubing integrity with repeated close ups. Finally, the configuration of the disposable cassette disclosed in Epstein requires more labor in assembly and replacement than the industry desires, raising the cost to health care consumers.

A second approach is described in Wunsch, U.S. Pat. No. 4,512,764. Wunsch discloses a three-piece manifold valve assembly infusion system capable of administering multiple solutions to a patient through a single supply tube. The manifold valve assembly includes a disposable tubing manifold with a single flexible trunk tube and a plurality of flexible branch tubes. Each flexible branch tube is connected to the flexible trunk tube on one end, and to a solution to be administered on its other end. The single flexible trunk tube is connected to a single intravenous supply catheter so that multiple solutions may be sequentially dispensed to the patient. Valves in the manifold valve assembly selectively engage each flexible branch tube, closing all but one branch tube at any one time, to prevent fluid flow through these branch tubes.

The Wunsch tubing manifold overcomes many of the problems associated with delivering multiple solutions to a patient, as well as some of the disadvantages of the disposable cassette disclosed in Epstein et al. For example, the flexibility of the trunk tube and branch tubes disclosed in Wunsch allows the tube paths to be pinched off with less force than is required in Epstein. This fact results in a more energy efficient system, since less energy is required to operate the valve mechanism. However, the disposable tubing manifold disclosed in Wunsch has disadvantages of its own. First, because of the necessary connections of flexible plastic tubing, the Wunsch manifold is difficult to fabricate. Second, because of the increased complexity in fabrication, the Wunsch flexible tubing manifold has increased costs associated with its manufacture. Finally, the tubing manifold disclosed in Wunsch requires more labor by the health care practitioner to replace than is desired in the industry.

Although the Wunsch and Epstein et al. patents attempt to meet the need for a system capable of administering multiple fluids to a patient through a single catheter supply tube, each of these disclosed methods has its own shortcomings and fails to satisfy a need in the infusion system market. The AVI pumping cassette, disclosed in U.S. Pat. Nos. 4,382,753 and 4,236,880, is the most reliable, accurate and potentially the most cost-effective disposable pumping cassette in the market place. However, it is designed to deliver a single IV solution to a patient at any one time.

SUMMARY OF THE INVENTION

The present invention is an integral disposable manifold and pump cassette through which fluid is pumped from inlet tubes to an outlet tube. The integral disposable manifold and pump cassette form a single disposable cassette which may be inserted into a single pump housing. The cassette includes first and second sheets of flexible plastic material. Sealed inlet channels are formed between the first and second sheets of flexible plastic material. The sealed inlet channels are connectable to the inlet tubes for fluid passage therethrough, and can be individually pinched closed to prevent fluid passage. A sealed main channel is also formed between the first and second sheets of flexible plastic material. The sealed main channel is connected between each of the sealed inlet channels and the outlet tube. A pumping chamber, formed between the first and second sheets of flexible plastic material as a portion of the main channel, connects the inlet channels to the outlet tube.

A flange, also formed between the first and second sheets of flexible material, surrounds the inlet channels, the main channel and the pumping chamber. The flange facilitates the insertion and removal of the single disposable manifold and pump cassette from the single pump housing. A first flexible diaphragm is formed in the first sheet of flexible plastic material. The first flexible diaphragm forms a portion of the pumping chamber.

DETAILED DESCRIPTION OF THE PREFERRED EMBODIMENTS

Figure 1A:
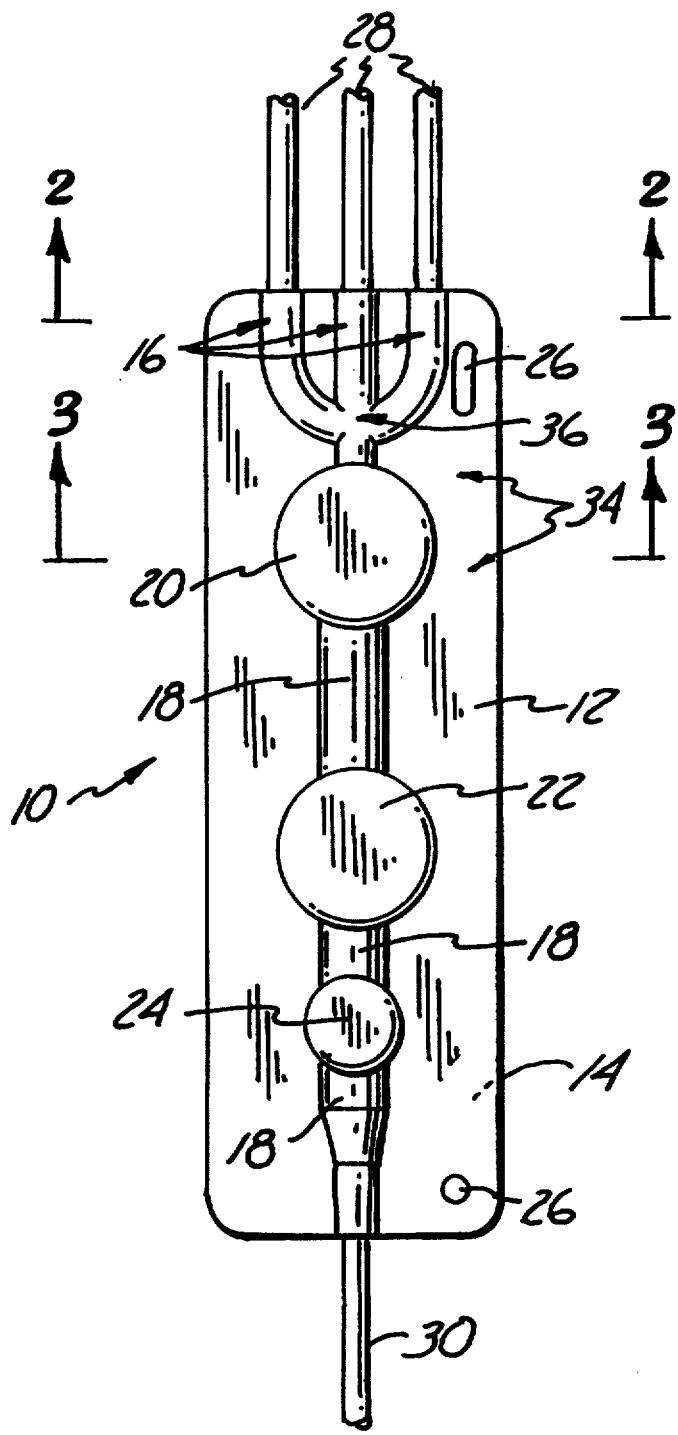
FIG. 1A is a back view of the disposable pumping cassette with integral manifold.
Figure 1B:
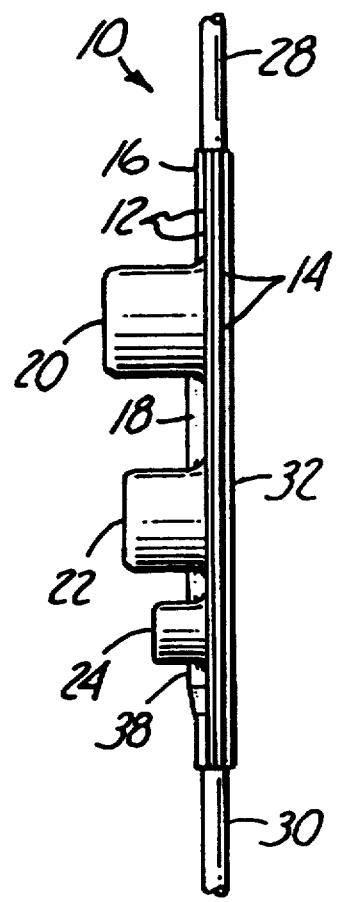
FIG. 1B is a side view of the disposable pumping cassette with integral manifold.

FIGS. 1A and 1B are back and side views of disposable pumping cassette with integral manifold 10 of the present invention. Disposable pumping cassette with integral manifold 10 is intended for use with volumetric infusion pump 60 (shown in FIGS. 4 and 5) for the administration of intravenous (IV) fluids to a patient. Pumps of this type are typically designed for use with IV tubing and a pumping cassette having flexible walls defining one or more fluid pumping chambers which may be compressed to regulate fluid flow through the IV tubing.

In the preferred embodiments of the present invention, disposable pumping cassette with integral manifold 10 includes two sheets, lower sheet 12 and upper sheet 14, which are preferably made out of a flexible plastic material which is capable of heat sealing. In one preferred embodiment, both lower sheet 12 and upper sheet 14 are formed of a vinyl plastic material.

Both lower sheet 12 and upper sheet 14 are vacuum formed or blow molded to define the passages and chambers of pumping cassette with integral manifold 10. Lower sheet 12 of disposable pumping cassette with integral manifold 10 has a raised portion 38 forming the bottom half of main flow channel 18 and inlet channels 16. Also formed in lower sheet 12 and extending downward (upward in the back view of FIG. 1A) is first flexible diaphragm pumping chamber 20. In one preferred embodiment of the present invention, lower sheet 12 also includes second flexible diaphragm pumping chamber 22, flexible diaphragm pressure sensing chamber 24, and alignment holes 26.

Upper sheet 14 is primarily a planar sheet, except for raised portion 32 which extends substantially the entire length of upper sheet 14. Raised portion 32 is the top half of inlet channels 16 and of main flow channel 18. Inlet channels 16 and main flow channel 18 carry fluid from inlet tubes 28 to outlet tube 30. The radii of inlet tubes 28 and outlet tube 30 are smaller than the radius of raised portion 32. Upper sheet 14 may also include alignment holes 26.

As stated previously, lower and upper sheets 12 and 14 are preferably made of a plastic material which is easily sealed by heat sealing. Sheets 12 and 14 are heat sealed together at the time of forming or in a subsequent operation. The mating surfaces of sheets 12 and 14 may be a material with a lower melting point therefore aiding the sealing process. Inlet tubing 28 and outlet tubing 30 are also preferably clear material which is heat sealed with lower and upper sheets 12 and 14.

Although heat sealing is one preferred means of sealing lower and upper sheets 12 and 14 together with tubing 28 and 30, sealing can also be accomplished by ultrasonic welding, RF sealing, solvent bonding, or by other sealing techniques.

In one preferred embodiment, disposable pumping cassette with integral manifold 10 is formed by blow molding. In this case, lower sheet 12 and upper sheet 14 are heat sealed together with tubing 28 and 30 at the time of the molding operation. The advantage of blow molding is that it avoids any registration problems which may be otherwise encountered in attempting to attach together separately molded lower and upper sheets 12 and 14.

In another preferred embodiment, tubing 28 and 30 is connected with inlet channels 16 and main flow channel 18 using the method disclosed in U.S. Pat. No. 5,203,943. This reference discloses an improved construction for a tubular member to facilitate the formation of a leak resistant connection in a fluid transport system. The reference also discloses a method for making such a connection.

Alternately, vacuum molding of the individual lower and upper sheets 12 and 14 may be used. In this embodiment, multiple cavity molds are used to produce molded plastic sheets containing many of the same parts (either sheet 12 or sheet 14). Tubes 28 and 30 are placed into position, and then a sheet having an identical number of the other parts is placed into position over the first sheet and the tubing. Next, sheets 12 and 14 are heat sealed together. Finally, the individual pump chambers are severed from one another by punch and dye type cutters. In this manner, a large number of disposable pump cassettes with integral manifolds 10 can be fabricated at the same time.

When lower sheet 12 and upper sheet 14 are sealed together, flange 34 is formed by the upper and lower sheets of flexible plastic material. Flange 34 generally surrounds inlet channels 16, main channel 18, pumping chambers 20 and 22, and pressure sensing chamber 24.

Cut in flange 34 are one or more registration or alignment holes 26 which have been punched out of sheets 12 and 14. Flange 34 facilitates easy insertion and removal of the single disposable pump cassette with integral manifold from a pump housing. Alignment holes 26 help the health care practitioner to accurately position cassette 10 within the pump housing (shown in FIGS. 4 and 5).

When cassette 10 is used with an infusion pump, each inlet channel 16 is connected through IV tubing 28 to a separate source of IV fluid. As will be discussed later, each inlet channel 16 may be individually pinched closed by a solenoid valve 59 to prevent the flow of fluid therethrough. The IV fluid received by one or more of inlet channels 16 flows through junction or bifurcation 36 into main flow channel 18. Flexible diaphragm pumping chambers 20 and 22 may be compressed by a pumping means to regulate the fluid flow through the cassette. In the embodiment illustrated in FIGS. 1A and 1B, flexible diaphragm pressure sensing chamber 24 is also provided so that pressure within cassette 10 may be assessed by a pressure transducer acting against the wall of chamber 24.

Figure 2:
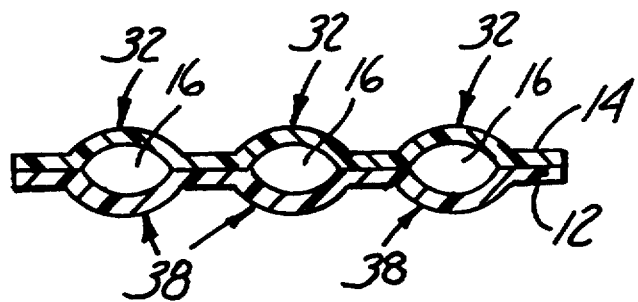
FIG. 2 is a sectional view of the multiple inlet channels of the pumping cassette with integral manifold.
Figure 3:
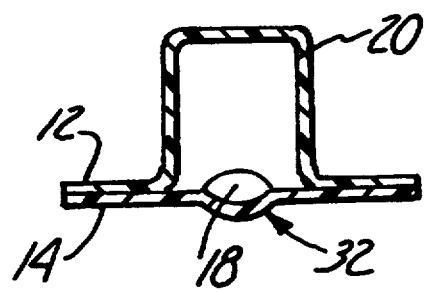
FIG. 3 is a sectional view of the main flow channel and flexible diaphragm pumping chamber of the pumping cassette with integral manifold.

FIGS. 2 and 3 show sectional views at different positions of disposable pump chamber with integral manifold 10. FIG. 2 is a sectional view of inlet channels 16 of disposable cassette 10. Inlet channels 16 are formed between raised portions 32 and 38 of upper and lower sheets 14 and 12. Because of the special cross-sectional shape of inlet channels 16, the channels may be pinched closed with a force which is much less than required in prior art cassettes. The low pinch-off force of inlet channels 16 ultimately results in a reduction of the energy needed to power the infusion pump solenoids 59 which pinch closed the inlet channels 16.

FIG. 3 is a sectional view of main flow channel 18 and flexible diaphragm pumping chamber 20 of the present invention. Raised portions 32 and 39 of lower and upper sheets 14 and 12 form main flow channel 18 and pumping chamber 39. Flexible pumping diaphragm 20 must be flexible enough to permit the diaphragm to be manipulated by a piston in the pump assembly.

Figure 5:
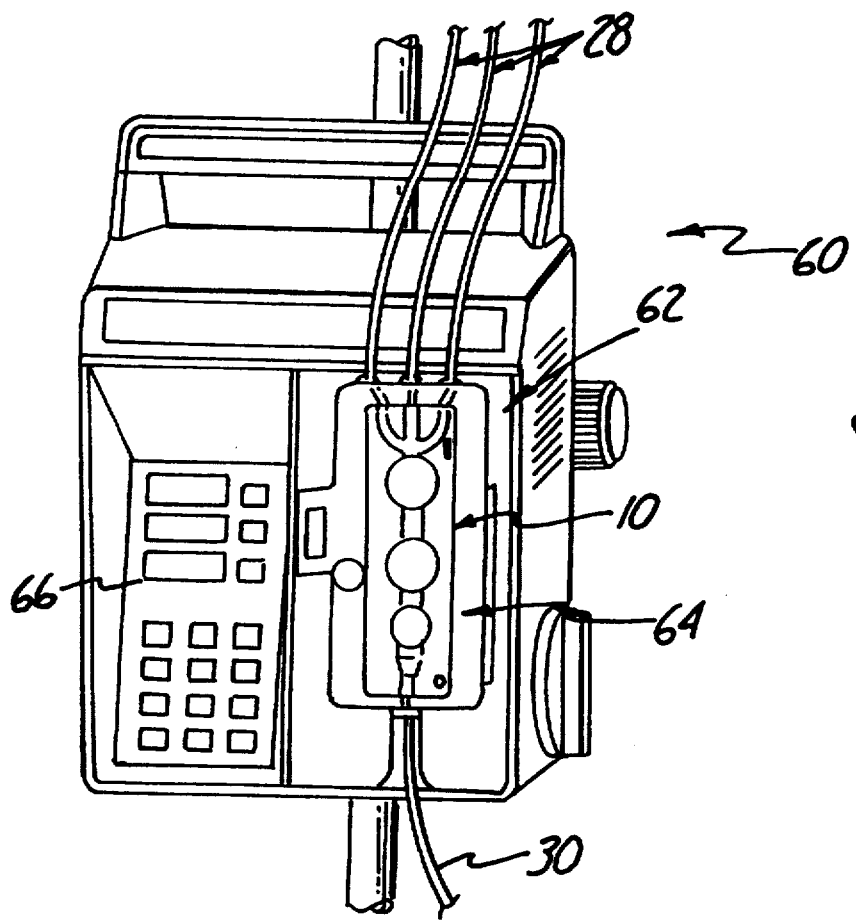
FIG. 5 is a perspective view of an infusion pump which may be used with the disposable pump cassette with integral manifold.
Figure 4:
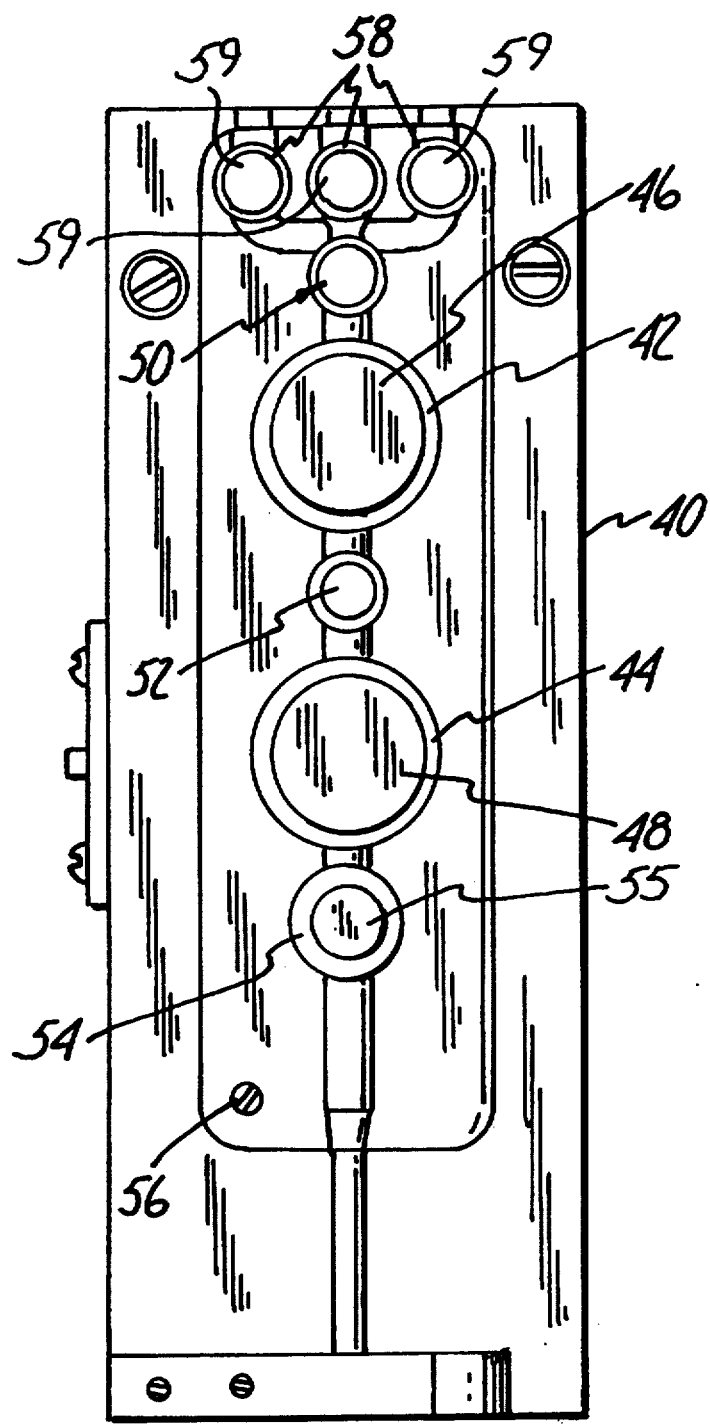
FIG. 4 is a view of a portion of the infusion pump assembly with a cassette receiving enclosure.
Figure 2:
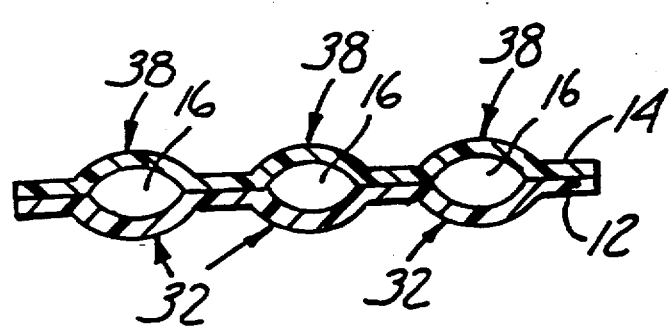
Figure 3:
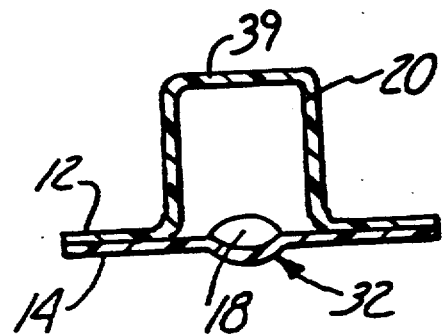

FIG. 4 shows a view of cassette receiving enclosure 40, which forms part of infusion pump assembly 60 (shown in FIG. 5). Cassette receiving enclosure 40 has first and second cylinders 42 and 44 in which first and second pistons 46 and 48 can be driven by a motor to manipulate the volume in pumping chambers 20 and 22 (FIGS. 1A and 1B). This causes fluid within the IV tubing to be pumped to the patient in a regulated manner. First and second valves 50 and 52 are also provided within enclosure 40 to seal main channel 18 at various locations in coordination with the movement of first and second pistons 46 and 48 during a pumping cycle. Within third cylinder 54 is third piston 55 which is not motor driven, but rather is movable in response to fluid pressure within chamber 24 to provide a pressure monitoring means. One or more alignment pins 56 may be provided to interact with alignment holes 26 (FIGS. 1A and 1B) of cassette 10 in order to facilitate proper positioning of the cassette within enclosure 40.

Cassette receiving enclosure 40 also includes cylinders 58 which house solenoid valves 59. Each solenoid valve 59 can be individually activated in order to pinch closed one of inlet channels 16. In this way, infusion pump 60 can allow fluid to be pumped through one or more of inlet channels 16 while preventing fluid flow through other inlet channels. This allows pump 60 to pump fluid from several inlet tubes 28 simultaneously. In the alternative, pump 60 may sequentially deliver, to the patient, fluid from one inlet tube 28 at a time.

FIG. 5 shows an infusion pump which may be used with the disposable pump cassette with integral manifold. Infusion pump 60 includes a pumping assembly shown generally at 62 employing the piston and solenoid pumping means, shown in FIG. 4, for pumping fluid through pump cassette with integral manifold 10 (not shown). Releasable holding assembly 64, along with cassette receiving enclosure 40 of FIG. 4, holds pump cassette with integral manifold 10 during operation of infusion pump 60. In a preferred embodiment, infusion pump 60 of the present invention is controlled by a microprocessor (not shown) connected to visual display and keypad 66. Visual display and keypad 66 allows a health care practitioner to interface with infusion pump 60. The microprocessor in an infusion pump according to the present invention has embedded programming so as to control the solenoid valves to permit the pumping of multiple IV solutions according to a predetermined plan. The microprocessor also includes programming which operates the visual display and keypad to allow the heath care practitioner to specify parameters of the predetermined plan. The exact programming steps required depend heavily on the microprocessor and display unit chosen.

The pumping cassette with integral manifold of the present invention provides many advantages over the prior art. Forming the pumping cassette with integral manifold between two sheets of flexible plastic material reduces the costs and complexity of fabricating the disposable cassette. The flange created by the two sheets of plastic material facilitates easy insertion and removal of the disposable cassette from the pump housing. The cross sectional shape of the inlet channels and main flow channel formed between the two sheets of flexible plastic material allows these channels 16 and 18 to be pinched closed with less force. This results in less wear on the channels and in increased energy efficiency. Finally, the multiple inlet channels 16 which can be individually pinched closed, allow multiple IV solutions to be administered to a patient with only a single IV venipuncture.

Although the present invention has been described with reference to preferred embodiments, workers skilled in the art will recognize that changes may be made in form and detail without departing from the spirit and scope of the invention. For example, the infusion pump could alternatively be of the type commonly referred to as "linear peristaltic pumps" which selectively squeeze straight portions of IV tubing to regulate or pump fluid through the tubing.

I claim:

1. A pump comprising:
 a disposable pump chamber through which fluid is pumped from a plurality of inlet tubes, the disposable pump chamber consisting of a first sheet of flexible plastic material and a second sheet of flexible plastic material sealed together to form therebetween a plurality of inlet channels which are connectable to the inlet tubes for fluid passage therethrough and which can be individually pinched closed to prevent fluid passage therethrough, the first and second sheets of flexible plastic material also forming a main flow channel which extends between the inlet channels and an outlet tube, wherein the main flow channel includes a flexible diaphragm pumping chamber, the first and second sheets of flexible plastic material also forming a flange generally surrounding the inlet channels, the main flow channel, and the flexible diaphragm pumping chamber, the inlet channels together having a single junction with the main flow channel bringing the inlet channels into fluid communication with the main flow channel;

a pump housing for receiving the disposable pump chamber;

a first cylinder in the pump housing positioned to be aligned with the flexible diaphragm pumping chamber;

a first piston movable in the first cylinder for acting on the flexible diaphragm pumping chamber;

valve means positioned in the pump housing for controlling fluid flow through each of the inlet channels; and drive means for causing relative motion of the first cylinder and the first piston to vary the volume of the flexible diaphragm pumping chamber.

2. The pump of claim 1 wherein the flexible material of the first and second sheets of the cassette holds the inlet channels in an open configuration to permit fluid passage therethrough but being resiliently flexible to permit the inlet channels to be individually pinched closed by the valve means to prevent fluid passage therethrough.

3. The pump of claim 1 further comprising: a main channel valve means for controlling fluid flow between the inlet and the flexible diaphragm pumping chamber.

4. The pump of claim 3 wherein the flange of the disposable pump chamber includes alignment holes which interact with alignment pins in the pump housing and facilitate proper positioning of the disposable pump chamber therein.

5. The pump of claim 4 wherein the valve means for controlling fluid flow comprises solenoid valves.

6. The pump of claim 1 wherein the sealed inlet channels are located at a first end of the disposable pump chamber and the outlet tube is located at a second end of the disposable pump chamber.

7. The pump of claim 6 wherein the main flow channel of the disposable pump chamber further comprises a flexible diaphragm pressure sensing chamber formed between the first and second sheets of flexible plastic material.

8. The pump of claim 7 further comprising a second cylinder in the pump housing positioned to be aligned with the flexible diaphragm pressure sensing chamber.

9. The pump of claim 8 further comprising a second piston movable in the second cylinder in response to fluid pressure within the flexible diaphragm pressure sensing chamber.

10. An integral disposable manifold and pump cassette through which fluid is pumped from a plurality of inlet tubes through a single outlet, the integral disposable manifold and pump cassette consisting of a first sheet of flexible plastic material and a second sheet of flexible plastic material sealed together to form therebetween:

a plurality of inlet channels sealingly connected to and in fluid communication with the inlet tubes, wherein the inlet channels can be individually pinched closed to prevent the flow of fluid therethrough;

a main flow channel which extends between the inlet channels and the outlet, the main flow channel including a first flexible diaphragm pumping chamber and a second flexible diaphragm pumping chamber, with the second flexible diaphragm pumping chamber positioned between the first flexible diaphragm pumping chamber and the outlet, the inlet channels together having a single junction with the main flow channel bringing the inlet channels into fluid communication with the main flow channel; and a flange generally surrounding the inlet channels and the main flow channel, the first sheet of flexible plastic material defining a first flexible diaphragm surrounded by the flange to form a portion of the first flexible diaphragm pumping chamber, and a second flexible diaphragm surrounded by the flange to form a portion of the second flexible diaphragm pumping chamber.

11. The integral disposable manifold and pump cassette of claim 10 wherein the flexible material of the first and second sheets holds the inlet channels in an open configuration to permit fluid passage therethrough but being resiliently flexible to permit the inlet channels to be individually pinched closed to prevent fluid passage therethrough.

12. An integral disposable manifold and pump cassette through which fluid is pumped from inlet tubes, the integral disposable manifold and pump cassette consisting essentially of a first sheet of flexible plastic material and a second sheet of flexible plastic material sealed together to form therebetween:

a plurality of inlet channels;

a main flow channel which extends between the inlet channels and an outlet, the inlet channels together having a single junction with the main flow channel bringing the inlet channels into fluid communication with the main flow channel; and a flange generally surrounding the inlet channels and the main flow channel, wherein the sealed inlet channels extend between the inlet tubes and the main flow channel, wherein the inlet channels can be individually pinched closed to prevent the flow of fluid therethrough, wherein the main flow channel includes a first flexible diaphragm pumping chamber and a second flexible diaphragm pumping chamber, wherein the second flexible diaphragm pumping chamber is positioned between the first flexible diaphragm pumping chamber and the outlet, wherein the first sheet of flexible plastic material has a first flexible diaphragm surrounded by the flange to form a portion of the first flexible diaphragm pumping chamber, and wherein the first sheet of flexible plastic material has a second flexible diaphragm surrounded by the flange to form a portion of the second flexible diaphragm pumping chamber.

13. The integral disposable manifold and pump cassette of claim 12 wherein the inlet channels are located at a first end of the flange and the outlet is located at a second end of the flange.

14. The integral disposable manifold and pump cassette of claim 13 wherein the main flow channel includes a flexible diaphragm pressure sensing chamber formed between the first and second sheet of flexible plastic material.

15. An integral disposable manifold and pump cassette through which fluid is pumped from a plurality of inlet tubes, the integral disposable manifold and pump cassette consisting essentially of a first sheet of flexible plastic material and a second sheet of flexible plastic material sealed together to form therebetween:

a plurality of inlet channels which are connectable to the inlet tubes for fluid passage therethrough and which can be individually pinched closed to prevent fluid passage therethrough;

a main flow channel which extends between the inlet channels and an outlet tube, wherein the main flow channel includes a flexible pumping chamber, the inlet channels together having a single junction with the main flow channel bringing the inlet channels into fluid communication with the main flow channel;

a flange generally surrounding the inlet channels, the main flow channel, and the flexible pumping chamber.

16. The integral disposable manifold and pump cassette of claim 15 wherein the inlet channels are located at a first end of the disposable manifold and pump cassette and the outlet tube is located at a second end of the disposable manifold and pump cassette.

17. The integral disposable manifold and pump cassette of claim 16 wherein the main flow channel includes a flexible pressure sensing chamber formed between the first and second sheets of flexible plastic material.

18. An integral disposable manifold and pump cassette through which fluid is pumped from inlet tubes, the integral disposable manifold and pump cassette forming a single disposable cassette which may be inserted into a single pump housing, the cassette consisting of:

a first sheet of flexible plastic material; and a second sheet of flexible plastic material, the first and second sheets of flexible plastic material being sealed together to form therebetween:

a plurality of inlet channels formed between the first and second sheets of flexible plastic material, the inlet channels being connectable to the inlet tubes for fluid passage therethrough and can be individually pinched closed to prevent fluid passage therethrough;

a main flow channel formed between the first and second sheets of flexible plastic material, the main channel connecting the inlet channels to an outlet tube, the inlet channels together having a single junction with the main flow channel bringing the inlet channels into fluid communication with the main flow channel; and a flange formed by the first and second sheets of flexible plastic material, the flange generally surrounding the inlet channels and the main channel, the flange facilitating the insertion and removal of the single disposable cassette to and from the pump housing.

19. The integral disposable manifold and pump cassette of claim 18 wherein the flexible material of the first and second sheets holds the inlet channels in an open configuration to permit fluid passage therethrough but being resiliently flexible to permit the inlet channels to be individually pinched closed to prevent fluid passage therethrough.

20. The integral disposable manifold and pump cassette of claim 18 wherein the inlet channels are located at a first end of the disposable manifold and pump cassette and the outlet tube is located at a second end of the disposable manifold and pump cassette.

21. The integral disposable manifold and pump cassette of claim 20 wherein the main flow channel includes a flexible diaphragm pressure sensing chamber formed between the first and second sheets of flexible plastic material.

22. The integral disposable manifold and pump cassette of claim 20 further comprising:

a pumping chamber formed between the first and second sheets of flexible plastic material as a portion of the main channel, the pumping chamber being defined by a first flexible diaphragm formed in the first sheet.

* * * * *

UNITED STATES PATENT AND TRADEMARK OFFICE
CERTIFICATE OF CORRECTION

PATENT NO.  : 5,429,485　　　　　　　　　　Page 1 of 3
DATED       : July 4, 1995
INVENTOR(S) : Larry H. Dodge It is certified that error appears in the above-indentified patent and that said Letters Patent is hereby corrected as shown below:

Drawing sheet consisting of Figs. 2 and 3, should be replaced with the drawing sheet consisting of Figs. 2 and 3, as shown on the attached page.

Signed and Sealed this

Eighteenth Day of June, 1996

Attest:

BRUCE LEHMAN

Attesting Officer　　　　Commissioner of Patents and Trademarks

UNITED STATES PATENT AND TRADEMARK OFFICE
CERTIFICATE OF CORRECTION

PATENT NO. : 5,429,485
DATED : July 4, 1995
INVENTOR(S) : Larry H. Dodge

It is certified that error appears in the above-indentified patent and that said Letters Patent is hereby corrected as shown below:

On the title page:

Under section [56] "References Cited" "U.S. Patent Documents" add the following:

4,637,817 1/1987 Archibald et al.

4,673,389 6/1987 Archibald et al.

4,673,390 6/1987 Archibald 4,705,506 11/1987 Archibald 4,714,463 12/1987 Archibald et al.

5,078,699 1/1992 Haber et al......604/250

Under section [56] "References Cited" "Other Publications"

"07/926,826" should read --07/626,826--.

Please replace Figures 2 and 3 with the attached sheet.

Col. 5, line 41, "20" should read --(also 20)--.